(12) United States Patent
Ramaswamy et al.

(10) Patent No.: US 12,070,352 B2
(45) Date of Patent: Aug. 27, 2024

(54) SYSTEM AND METHOD FOR UTILIZING A SINGLE ULTRASOUND IMAGING DEVICE TO SIMULTANEOUSLY MEASURE A MATERNAL HEART RATE AND FETAL HEART RATES OF MULTIPLE FETUSES

(71) Applicant: GE Precision Healthcare LLC, Wauwatosa, WI (US)

(72) Inventors: Sivaramanivas Ramaswamy, Bangalore (IN); Vijith Venugopalan, Bangalore (IN); Kiran Kumar Bogineni, Bangalore (IN); Nagapriya Kavoori Sethumadhavan, Bangalore (IN); Steven Mitchell Falk, Baltimore, MD (US); Dianne Kessler, Brentwood, TN (US); Tamara Grassle, Wickenburg, AZ (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 0 days.

(21) Appl. No.: 17/836,238

(22) Filed: Jun. 9, 2022

(65) Prior Publication Data
US 2023/0397903 A1    Dec. 14, 2023

(51) Int. Cl.
*A61B 8/08*    (2006.01)
*A61B 8/00*    (2006.01)
(Continued)

(52) U.S. Cl.
CPC .............. *A61B 8/0866* (2013.01); *A61B 8/02* (2013.01); *A61B 8/4227* (2013.01);
(Continued)

(58) Field of Classification Search
CPC ....... A61B 8/0866; A61B 8/02; A61B 8/4227; A61B 8/4472; A61B 8/4477; A61B 8/4488; A61B 8/14; A61B 8/488
See application file for complete search history.

(56) References Cited

U.S. PATENT DOCUMENTS

2003/0139664 A1*   7/2003   Hunt .................. G01S 7/52023
                                                     600/407
2005/0251044 A1*   11/2005   Hoctor ................ B06B 1/0292
                                                     600/443

(Continued)

FOREIGN PATENT DOCUMENTS

CN          104905819 A      9/2015
WO      WO2021030145    *    2/2021

OTHER PUBLICATIONS

CN104905819 English Abstract; Espacenet search results; dated Jan. 12, 2024; 1 page.

(Continued)

*Primary Examiner* — Alexei Bykhovski
(74) *Attorney, Agent, or Firm* — Fletcher Yoder P.C.

(57) ABSTRACT

An ultrasound system includes a single transducer. The single transducer includes a flexible substrate. The single transducer also includes an array of transducer elements disposed on the flexible substrate and configured to be disposed on an abdomen of a subject having one or more fetuses disposed within a single uterus and to acquire scan data. The ultrasound system also includes a processor coupled to the single transducer and configured to receive the scan data and to determine a respective fetal heart rate of each fetus of the one or more fetuses based on the scan data.

14 Claims, 6 Drawing Sheets

(51) Int. Cl.
*A61B 8/02* (2006.01)
*A61B 8/14* (2006.01)

(52) U.S. Cl.
CPC .......... *A61B 8/4472* (2013.01); *A61B 8/4477* (2013.01); *A61B 8/4488* (2013.01); *A61B 8/14* (2013.01); *A61B 8/488* (2013.01)

(56) References Cited

U.S. PATENT DOCUMENTS

| | | | |
|---|---|---|---|
| 2013/0123636 A1* | 5/2013 | Longmore | A61B 8/02 600/459 |
| 2013/0261464 A1 | 10/2013 | Singh | |
| 2019/0021614 A1* | 1/2019 | Aarts | A61B 5/681 |
| 2019/0353764 A1* | 11/2019 | Vignon | G01S 7/52046 |
| 2020/0205784 A1* | 7/2020 | Wissel | A61B 8/5253 |
| 2021/0059538 A1* | 3/2021 | Kumar | A61B 5/053 |
| 2021/0059634 A1* | 3/2021 | Hamelmann | A61B 8/0866 |
| 2022/0028104 A1* | 1/2022 | Ebata | A61B 8/5223 |

OTHER PUBLICATIONS

EP application 23174896.3 filed May 23, 2023—extended Search Report dated Oct. 17, 2023; 8 pages.

* cited by examiner

SYSTEM AND METHOD FOR UTILIZING A SINGLE ULTRASOUND IMAGING DEVICE TO SIMULTANEOUSLY MEASURE A MATERNAL HEART RATE AND FETAL HEART RATES OF MULTIPLE FETUSES

BACKGROUND

The subject matter disclosed herein relates to medical imaging and, in particular, utilizing a single ultrasound imaging device to simultaneously measure a maternal heart rate and fetal heart rates of multiple fetuses.

An ultrasound device may be used for imaging targets such as organs and soft tissues in a human body, as well non-human targets. For example, an ultrasound device may be used for applications such as ultrasound/acoustic sensing, non-destructive evaluation (NDE), ultrasound therapy (e.g., High Intensity Focused Ultrasound (HIFU)), etc., in addition to ultrasound imaging of humans, animals, etc.

Ultrasound devices may use real time, non-invasive high frequency sound waves to produce a series of two-dimensional (2D) and/or three-dimensional (3D) images. The sound waves may be transmitted by a transmit transducer, and the reflections of the transmitted sound waves may be received by a receive transducer. The received sound waves may then be processed to display an image of the target. Ultrasound devices may also be utilized to monitor the heart rate of a fetus. Typically, a bulky ultrasound transducer is disposed (e.g., strapped) on the abdomen of the patient. In cases involving multiple fetuses within a uterus, multiple bulky ultrasound transducers (e.g., one for each fetus) are disposed on the abdomen of the patient. This may be very uncomfortable for the patient. In addition, if a fetus moves, one or more of the transducers must be repositioned on the patient. Further, if a fetus moves, it may be difficult to distinguish if the heart rate obtained belongs to the patient or the fetus.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In one embodiment, an ultrasound system is provided. The ultrasound system includes a single transducer. The single transducer includes a flexible substrate. The single transducer also includes an array of transducer elements disposed on the flexible substrate and configured to be disposed on an abdomen of a subject having one or more fetuses disposed within a single uterus and to acquire scan data. The ultrasound system also includes a processor coupled to the single transducer and configured to receive the scan data and to determine a respective fetal heart rate of each fetus of the one or more fetuses based on the scan data.

In another embodiment, a transducer for an ultrasound system is provided. The transducer includes a flexible substrate. The transducer also includes an array of transducer elements disposed on the flexible substrate and configured to be disposed on an abdomen of a subject having one or more fetuses disposed within a single uterus and to acquire scan data for determining a respective fetal heart rate of each fetus of the one or more fetuses based on the scan data.

In a further embodiment, a method for simultaneously monitoring fetal heart rate in a plurality of fetuses in a uterus is provided. The method includes providing, via a processor, signals to a single transducer to cause different subsets of transducer elements of the single transducer to sequentially capture scan data, wherein the single transducer comprises a flexible substrate and a flexible array having the transducer elements disposed on the flexible substrate. The method also includes receiving, at the processor, the scan data. The method further includes determining a respective location of each fetus of the plurality of fetuses based on the scan data. The method yet further includes applying, via the processor, Doppler shifts to the scan data. The method still further includes determining, via the processor, a respective fetal heart rate of each fetus of the plurality of fetuses based on the scan data with the Doppler shifts applied.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein.

DETAILED DESCRIPTION

Figure 1:
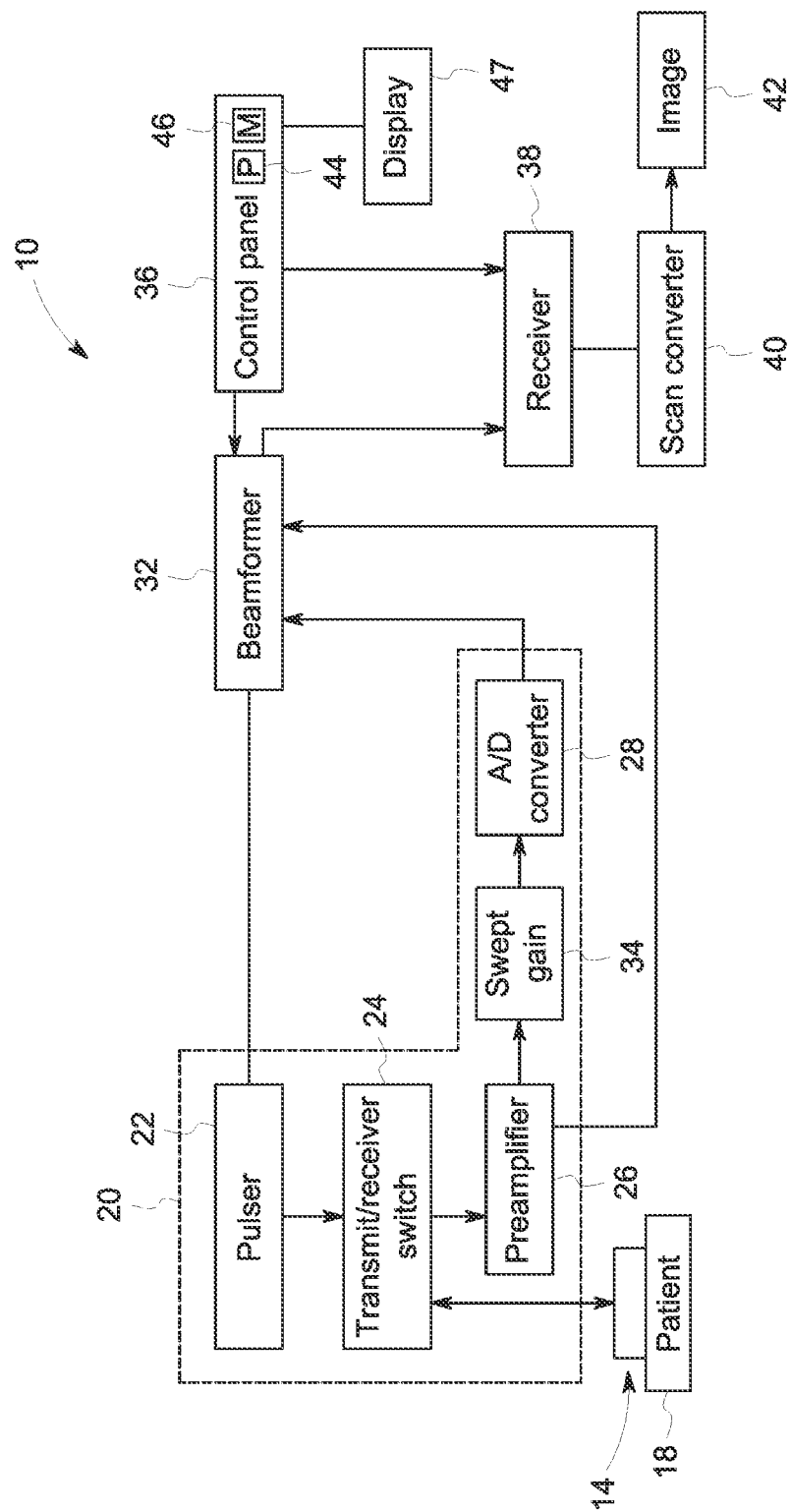
FIG. 1 is an embodiment of a block diagram of an ultrasound system, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

The present disclosure provides for systems and methods for simultaneously monitoring maternal heart rate and multiple fetal heart rates of multiple fetuses disposed within a single uterus of a patient. In particular, a single transducer may be utilized to continuously monitor the maternal heart rate and the multiple fetal heart rates without having to adjust a position of the single transducer even if one or more of the fetuses move. The single transducer is a wearable device having a flexible substrate and a flexible array of transducer elements disposed on the wearable device. In certain embodiments, the flexible substrate may a stretchable mesh having respective openings disposed on the superior end and the inferior end so that flexible substrate (i.e., the single transducer) may be slipped on the patient and slid to position the single transducer on the abdomen. The single transducer is coupled to a computing device or processing device that provides control signals to the single transducer and receives data from the single transducer via a wired or wireless connection. The ultrasound system is configured to determine a location of each fetus (in particular, a heart of each fetus) of the multiple fetuses and focus on each fetus to determine/measure a fetal heart rate of each fetus while also determining the maternal heat rate, thus, keeping the maternal heart rate distinct from the fetal heart rates. A combination of sub-aperture full matrix capture (FMC) of data (i.e., capturing matrix data for a group of transducer elements in an array) and total focusing method (TFM) reconstruction (i.e., reconstructing an image based on an A-scan matrix from the FMC) of the data may be utilized to localize the fetuses. In certain embodiments, inter-frame motion estimation metrics from B-mode images, such as block-matching, phase-based or optical flow vector-based tracking, may be utilized to localize the fetuses. The ultrasound system utilizes different algorithms to change where to focus with the transducer elements and/or a timing of data acquisition with the transducer elements to keep locked on to the fetuses for monitoring without having to change the position of the single transducer. The single transducer provides a more comfortable experience for the patient during the monitoring of the different heart rates and avoids having to utilize multiple bulky ultrasound transducers that need to be often readjusted.

With the preceding in mind, and by way of providing useful context, FIG. 1 depicts a high-level view of components of an ultrasound system 10 that may be employed in accordance with the present approach. The illustrated ultrasound system 10 includes a transducer array 14 (e.g., single transducer) having transducer elements (e.g., piezoelectric crystals) suitable for contact with a subject or patient 18 during an imaging procedure. The transducer array 14 may be configured as a two-way transducer capable of transmitting ultrasound waves into and receiving such energy from the subject or patient 18. In such an implementation, in the transmission mode the transducer array elements convert electrical energy into ultrasound waves and transmit it into the patient 18. In reception mode, the transducer array elements convert the ultrasound energy received from the patient 18 (backscattered waves) into electrical signals (or ultrasound data).

Each transducer element is associated with respective transducer circuitry, which may be provided as one or more application specific integrated circuits (ASICs) 20, which (although depicted outside the transducer array 14) may be present in (e.g., in the housing of) the transducer array 14. That is, each transducer element in the array 14 is electrically connected to a respective pulser 22, transmit/receive switch 24, preamplifier 26, swept gain 34, and/or analog to digital (A/D) converter 28 provided as part of or on an ASIC 20. In other implementations, this arrangement may be simplified or otherwise changed. For example, components shown in the circuitry 20 may be provided upstream or downstream of the depicted arrangement, however, the basic functionality depicted will typically still be provided for each transducer element. In the depicted example, the referenced circuit functions are conceptualized as being implemented on a single ASIC 20 (denoted by dashed line), however it may be appreciated that some or all of these functions may be provided on the same or different integrated circuits. The transducer circuitry may be used to control the switching of the transducer elements. The transducer circuitry may also be used to group the transducer elements into one or more sub-apertures (e.g., in response to control signals from the control panel 36).

Also depicted in FIG. 1, a variety of other imaging components are provided to enable image formation with the ultrasound system 10. Specifically, the depicted example of an ultrasound system 10 also includes a beam-former 32, a control panel 36, a receiver 38, and a scan converter 40 that cooperate with the transducer circuitry to produce an image or series of images 42 that may be stored and/or displayed to an operator or otherwise processed as discussed herein. The transducer array 14 may be communicate the ultrasound data to the beam-former via a wired connection or wireless connection (e.g., via a wireless communication unit that is part of the transducer array that communicates over a wi-fi network, utilizing Bluetooth® technique, or some other manner). A processing component 44 (e.g., a microprocessor) and a memory 46 of the system 10, such as may be present in control panel 36, may be used to execute stored routines for processing the acquired ultrasound signals to generate meaningful images and/or motion frames, which may be displayed on a display 47 of the ultrasound system 10. The processing component 44 may also localize multiple fetuses within a uterus of a patient and determine respective fetal heart rates of the fetuses and the maternal heart rate of the patient 18. The processing component 44 (in response to movement of a fetus) may utilize one or more algorithms (e.g., stored in the memory 46) to alter where to focus the transducer elements and/or a firing sequence (timing) for triggering the transducer elements.

Ultrasound information may be processed by other or different mode-related modules (e.g., B-mode, Color Doppler, power Doppler, M-mode, spectral Doppler anatomical M-mode, strain, strain rate, and the like) to form 2D or 3D data sets of image frames and the like. For example, one or more modules may generate B-mode, color Doppler, power Doppler, M-mode, anatomical M-mode, strain, strain rate, spectral Doppler image frames and combinations thereof, and the like. The image frames are stored and timing information indicating a time at which the image frame was acquired in memory may be recorded with each image frame. The modules may include, for example, a scan conversion module to perform scan conversion operations to convert the image frames from Polar to Cartesian coordinates. A video processor module may be provided that reads the image frames from a memory and displays the image frames in real time while a procedure is being carried out on a patient. A video processor module may store the image frames in an image memory, from which the images are read and displayed. The ultrasound system 10 shown may comprise a console system, or a portable system, such as a hand-held or laptop-type system.

The ultrasound system 10 may be operable to continuously acquire ultrasound scan data at a frame rate that is suitable for the imaging situation in question. Typical frame rates may range from 20-120 but may be lower or higher. The acquired ultrasound scan data may be displayed on the display 47 at a display-rate that can be the same as the frame rate, or slower or faster. An image buffer may be included for storing processed frames of acquired ultrasound scan data that are not scheduled to be displayed immediately. Preferably, the image buffer is of sufficient capacity to store at least several minutes worth of frames of ultrasound scan data. The frames of ultrasound scan data are stored in a manner to facilitate retrieval thereof according to its order or time of acquisition. The image buffer may be embodied as any known data storage medium.

The display 47 may be any device capable of communicating visual information to a user. For example, the display 47 may include a liquid crystal display, a light emitting diode display, and/or any suitable display or displays. The display 47 can be operable to present ultrasound images and/or any suitable information.

Components of the ultrasound system 10 may be implemented in software, hardware, firmware, and/or the like. The various components of the ultrasound system 10 may be communicatively linked. Components of the ultrasound system 10 may be implemented separately and/or integrated in various forms.

Figure 2:
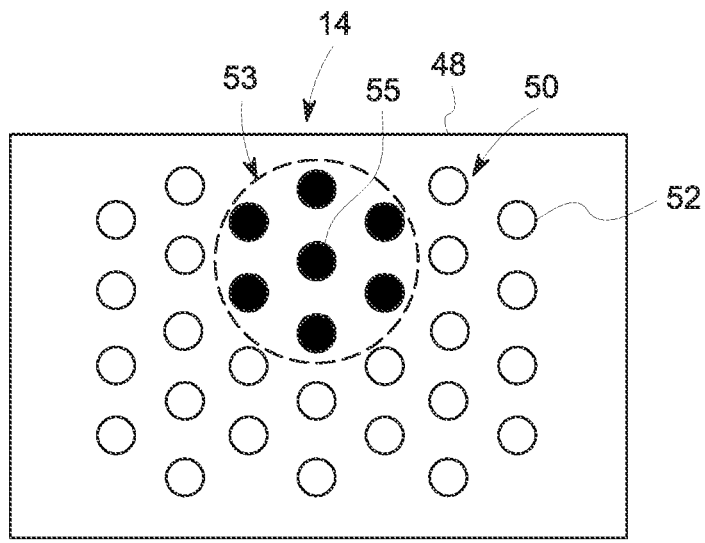
FIG. 2 is a schematic diagram of a transducer, in accordance with aspects of the present disclosure.

FIG. 2 is a schematic diagram of the transducer 14 (e.g., single transducer). The transducer 14 includes a flexible substrate 48 and a flexible array 50 of transducer elements 52 (e.g., piezoelectric crystals). In certain embodiments, the transducer elements 52 may be made of lead zirconate titanate (PZT). The number of transducer elements 52 forming the flexible array 50 may vary from 10 to 100 or more transducer elements 52. During operation, the transducer elements 52 function to acquire data for locating multiple fetuses within a uterus and/or measuring heart rates (e.g., maternal heart rate and fetal heart rate of each fetus). Different subsets (e.g., 2 or more transducer elements 52 but less than the total number of transducer elements 52 that form the array 50) of the transducer elements 52 are triggered or fired sequentially (i.e., to transmit ultrasound waves). Thus, one subset of transducer elements 52 may be fired or triggered, then a different subset of transducer elements 52 may be fired or triggered, and the firing sequence continues until each of the transducer elements 52 have been fired or triggered. In certain embodiments, the data is acquired utilizing sub-aperture FMC. In certain embodiments, the data is acquired in low resolution B-mode to localize and track fetal movement (e.g., where individual rows of transducer elements 52 are sequentially fired with each subsequent fired row being adjacent to the previously fired row). In certain embodiments multi-plane low resolution B-mode images are reconstructed to localize fetuses. In certain embodiments, the transducer elements 52 may be sequentially fired or triggered individually (as opposed to with a subset). The different subsets may have the same number of transducer elements 52 or vary in the number of transducer elements 52 making up the subset. All transducer elements 52 of the array 50 receive the ultrasound energy returned from the patient. For example, assume 6 of the transducer elements 52 form a subset 53 of transducer elements 52 and transducer element 55 of the subset 53 transmits ultrasound waves, then transducer element 55, the rest of the subset 53 of transducer elements 52, and all of the transducer elements 52 outside the subset 53 receive the ultrasound energy returned from the patient. The layout of the transducer elements 52 as depicted is two-dimensional (2D) scaled. This utilization of the transducer elements 52 ensures sufficient depth of field for Doppler measurements to enable measurement of the heart rates (e.g., fetal and maternal). As described in greater detail below, the acquisition of scan data from the sequential firing of the transducer elements enables the localization of the different fetuses within the uterus. In addition, as described in greater detail below, adjusting where to focus the transducer elements 52 and/or changing the firing sequence (e.g., timing) of the transducer elements 52 enables the transducer 14 to be kept in place (i.e. not readjusting the transducer's position) when one or more fetuses move.

Figure 3:
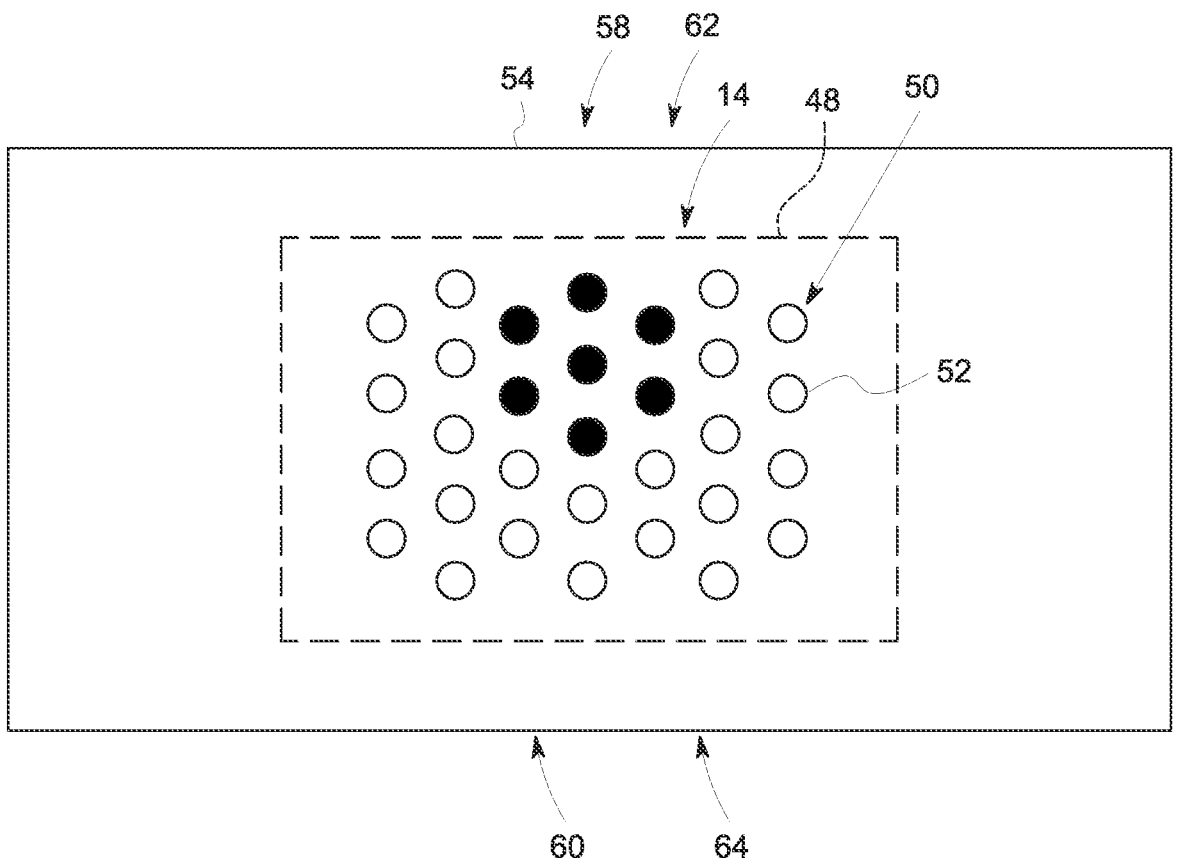
FIG. 3 is a schematic diagram of a belt having the transducer in FIG. 2, in accordance with aspects of the present disclosure.
Figure 4:
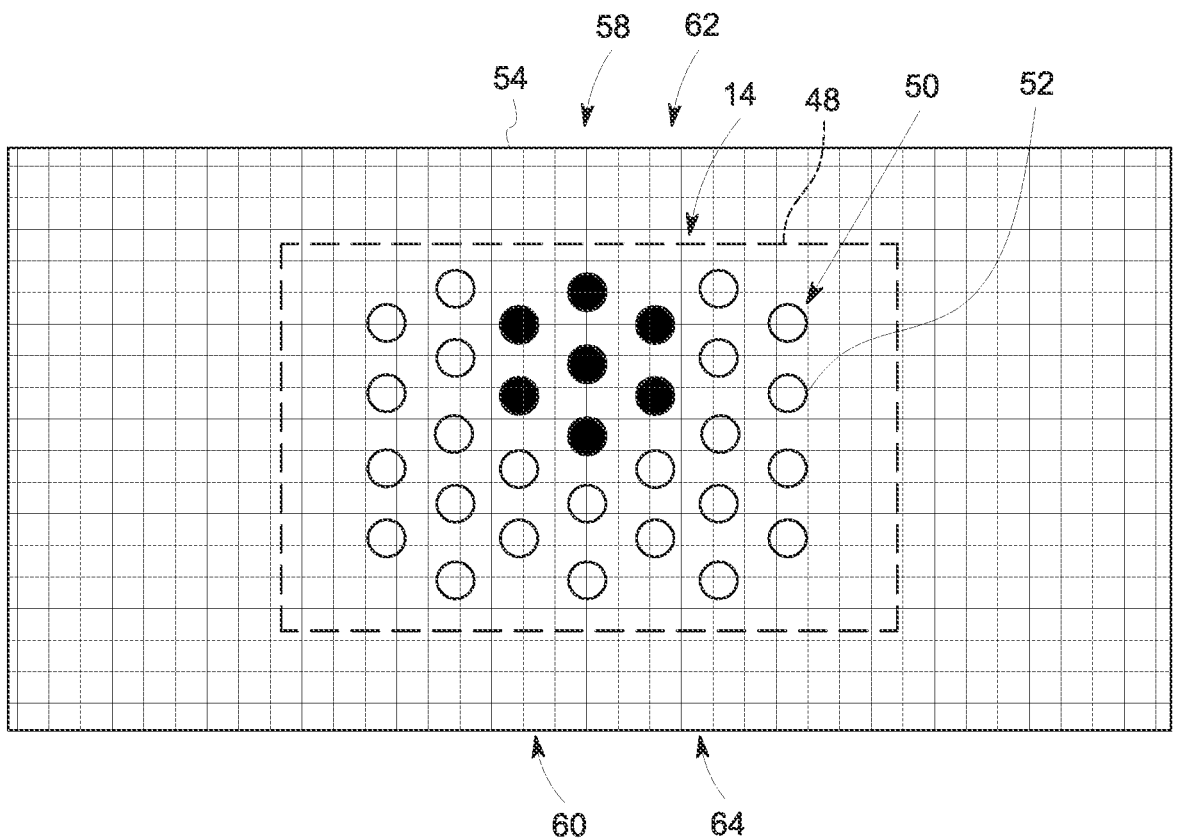
FIG. 4 is a schematic diagram of a belt (e.g., having a mesh material) having the transducer in FIG. 2, in accordance with aspects of the present disclosure.
Figure 5:
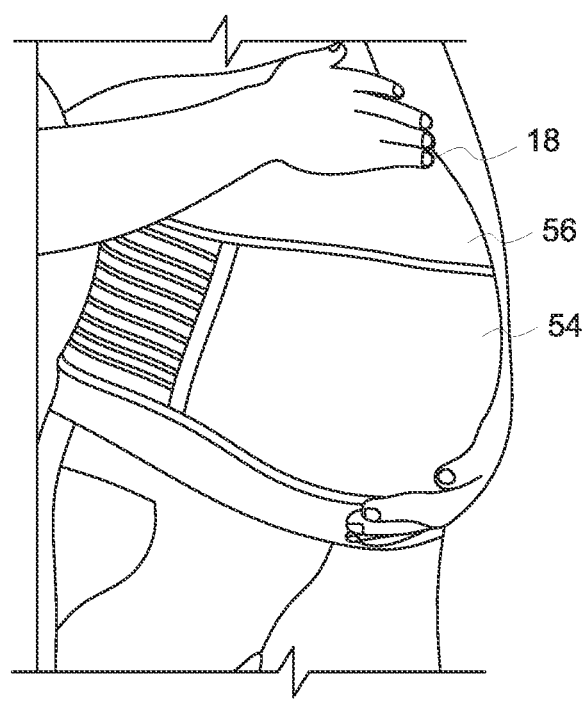
FIG. 5 is a schematic diagram of a belt having the transducer in FIG. 2 disposed about an abdomen of a pregnant patient, in accordance with aspects of the present disclosure.

As depicted in FIG. 3, the flexible substrate 48 may be part of a single flexible belt 54 that is configured to be disposed about the abdomen of the patient (e.g., such as flexible belt 54 in FIG. 5 disposed about an abdomen 56 of a pregnant patient 18). The flexible substrate 48 may be part of the belt 54 or coupled to the belt 54. The transducer 14 is disposed on an inner surface of the belt 54 and oriented so that the transducer elements 54 face the abdomen. The flexible belt 54 may be designed to be comfortable on the patient. For example, the flexible belt 54 may be made of a stretchable mesh material, as shown in FIG. 4 (e.g., similar to the material utilized with postpartum underwear), that is thin, soft, breathable, and cool. The flexible belt 54 may also be stretchy so as to conform to the different sizes of patients. In certain embodiments, the flexible belt 54 may have full openings 58, 60 on respective ends 62, 64 (e.g., superior and inferior ends) to enable the flexible belt 54 to be slid along the patient's body until is disposed about the abdomen. In certain embodiments, the flexible belt 54 may be adjustable for fit and wrapped around the abdomen of the patient (e.g., similar to abdominal binders) and secured via fasteners (e.g., hook and loop fasteners).

Figure 6:
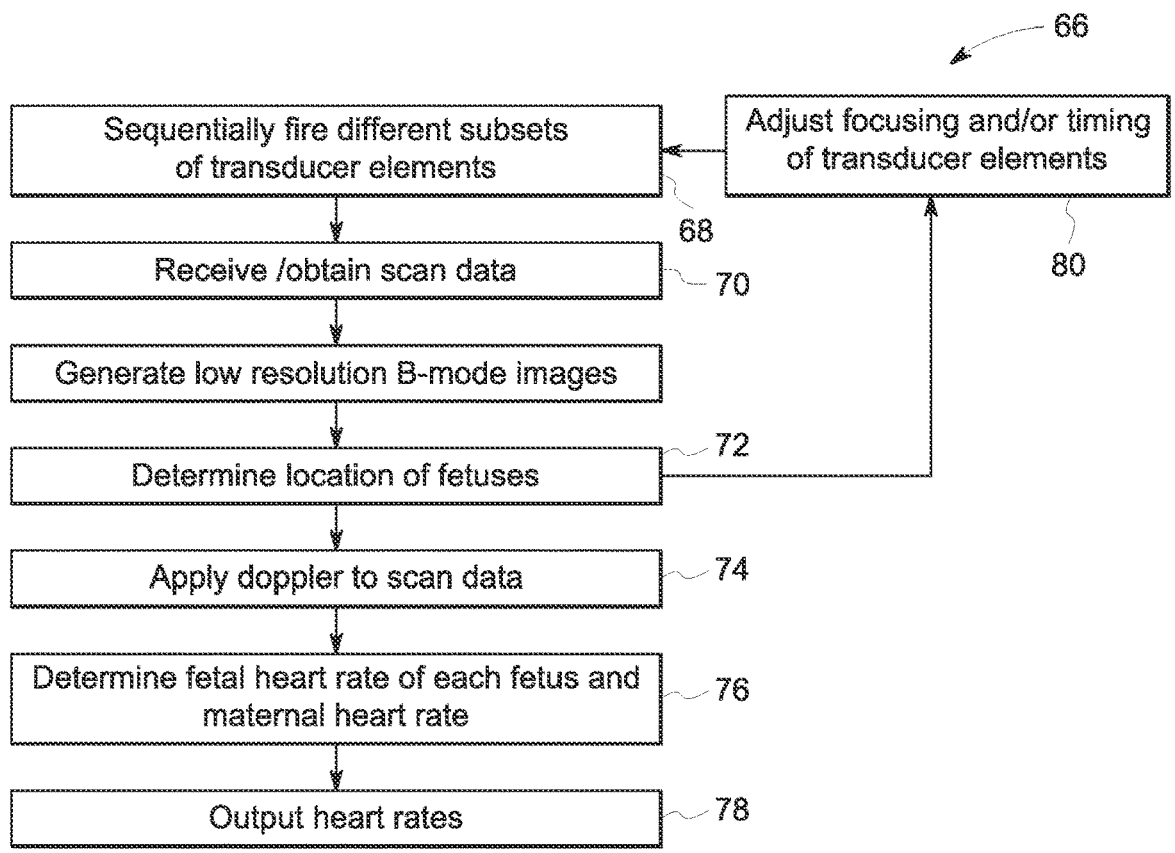
FIG. 6 is a flow chart of a method for simultaneously monitoring fetal heart rate in a plurality of fetuses in a uterus, in accordance with aspects of the present disclosure.

FIG. 6 is a flow chart of a method 66 for simultaneously monitoring fetal heart rate in a plurality of fetuses in a uterus (and maternal heart rate). The method 66 may be performed by the control panel 36 (e.g., processing component 44) of the ultrasound system 10 in FIG. 1. The method 66 includes sequentially firing different subsets of transducer elements from a single transducer (e.g., transducer 14 in FIG. 2) to capture scan data (e.g., ultrasound data) (block 68). In particular, the single transducer receives signals (e.g., control signals) for sequentially firing the different subsets of transducer elements for transmission and reception. As noted above, the firing sequence continues until each transducer element has been fired or triggered. In certain embodiments, individual transducer elements may be sequentially fired or triggered individually. The method 66 also includes receiving or obtaining the scan data from the single transducer (block 70).

The method 66 also includes generating (reconstructing) low-resolution B-mode images or image datasets from the scan data for localizing fetuses (block 71). The image dataset is generated along multiple planes utilizing the flexible array 50 of transducer elements 52 in FIG. 2. The method 66 further includes determining a respective location (e.g., source location) of each fetus (e.g., fetal heart) of multiple fetuses disposed within the uterus of a patient (block 72) in the reconstructed images.

The method 66 still further includes applying Doppler shift to the scan data (block 74). Upon applying the Doppler shift, the method 66 includes determining a respective fetal heart rate for each fetus in the uterus and the maternal heart rate of the patient (block 76). The maternal heart rate is distinguishable from the fetal heart rates since the location of the maternal heart rate will remain stationary relative to the single transducer. The fetal heart rate and maternal heartrate are distinguishable based on the location information available from the reconstructed images, thus, enabling time-gating or windowing of the signal. Therefore, the maternal heart rate will not be confused with the fetal heart rates. The method 66 also includes outputting the heart rates (e.g., fetal heart rates and maternal heart rate) (block 78). For example, the heart rates may be shown on a display of the ultrasound system (e.g., display 47 in FIG. 1) or a remote display.

In certain embodiments, when one or more of the fetuses in the uterus moves, the method 66 includes adjusting (e.g., via one or more algorithms) the focusing of the transducer elements and/or the timing (e.g. of the firing or triggering) of the transducer elements (block 80). Once a location is known, the beamforming algorithm will be tuned to focus at different regions. For example, a beam forming algorithm adjusts the time delay for transmission and reception to focus at a particular location. Fetal localization data (from block 72) is used to guide changes to the focal laws (i.e., mathematical formulas utilized for firing) to focus the beams. This enables the fetal heart rates of all of the fetuses to be simultaneously and continuously monitored even when the fetuses move. In addition, this avoids having to reposition the single transducer (and belt) to accommodate for movement of the fetuses.

Figure 7:
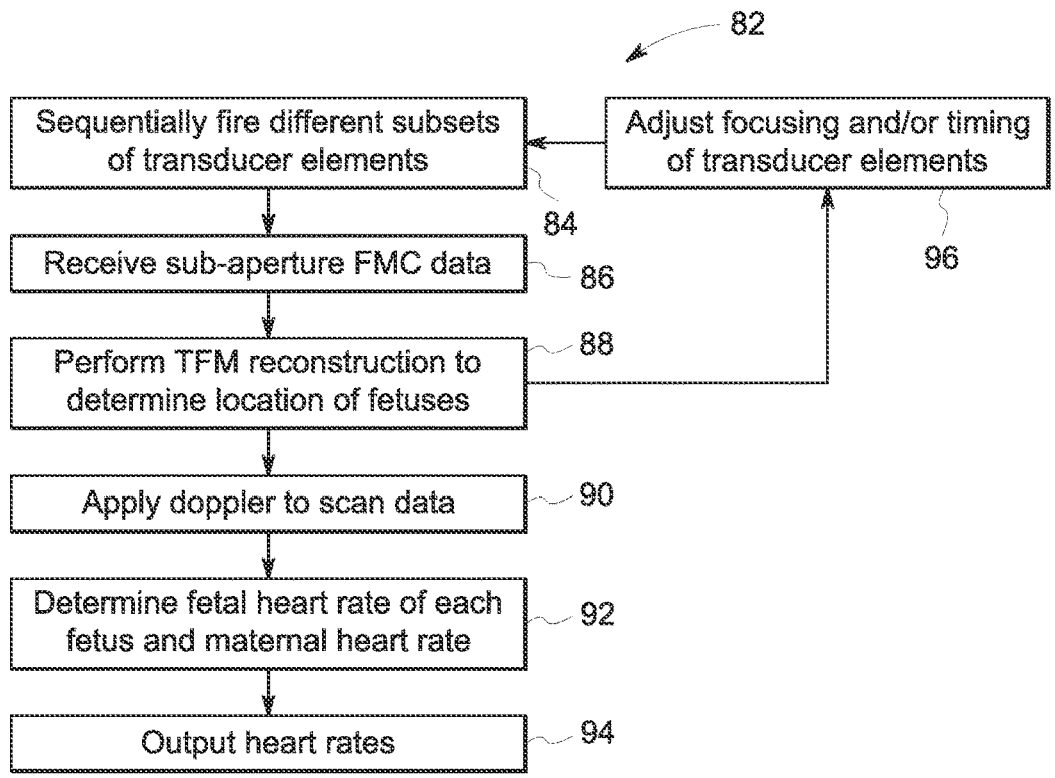
FIG. 7 is a flow chart of a method for simultaneously monitoring fetal heart rate in a plurality of fetuses in a uterus (e.g., utilizing both sub-aperture full matrix capture (FMC) and total focusing method (TFM) reconstruction for tracking), in accordance with aspects of the present disclosure.

FIG. 7 is a flow chart of a method 82 for simultaneously monitoring fetal heart rate in a plurality of fetuses in a uterus (e.g., utilizing both sub-aperture FMC and TFM reconstruction for tracking). The method 82 may be performed by the control panel 36 (e.g., processing component 44) of the ultrasound system 10 in FIG. 1. The method 82 includes sequentially firing different subsets of transducer elements from a single transducer (e.g., transducer 14 in FIG. 2) to capture scan data (e.g., sub-aperture FMC data for different subsets of transducer elements) (block 84). In particular, the single transducer receives signals (e.g., control signals) for sequentially firing the different subsets of transducer elements. As noted above, the firing sequence continues until each transducer element has been fired or triggered. In certain embodiments, individual transducer elements may be sequentially fired or triggered individually. The method 82 also includes receiving or obtaining the sub-aperture FMC data from the single transducer (block 86).

The method 82 further includes performing TFM reconstruction on the sub-aperture FMC data to determine a respective location (e.g., source location) of each fetus (e.g., fetal heart) of multiple fetuses disposed within the uterus of a patient (block 88). TFM enables simultaneous reconstructions for all depths. In one embodiment, each element (one by one) of the array transmits and all elements of the array receive and the process is cycled so that all of the elements of the array eventually act as a transmitter (i.e., FMC). Depending upon the location to focus, the beams are summed to reconstruct the image. In certain embodiments, the beam may be focused in the entire region of interest and an image generated. TFM involves summing the elementary A-scan signals from all elements in the array to generate a frame of pixels where each individual pixel is computed using a dedicated focal law. These frames can be used for "live" interpretation or they can be stored for each position of the probe, similar to a "dynamic" merge view in regular phased array.

The method 82 still further includes applying Doppler shift to the scan data (block 90). Upon applying the Doppler shift, the method 82 includes determining a respective fetal heart rate for each fetus in the uterus and the maternal heart rate of the patient (block 92). The maternal heart rate is distinguishable from the fetal heart rates since the location of the maternal heart rate will remain stationary relative to the single transducer. Thus, the maternal heart rate will not be confused with the fetal heart rates. The method 82 also includes outputting the heart rates (e.g., fetal heart rates and maternal heart rate) (block 94). For example, the heart rates may be shown on a display of the ultrasound system (e.g., display 47 in FIG. 1) or a remote display.

In certain embodiments, when one or more of the fetuses in the uterus moves, the method 82 includes adjusting (e.g., via one or more algorithms) the focusing of the transducer elements and/or the timing (e.g., of the firing or triggering) of the transducer elements (block 96). Fetal location dataset (from block 88) is used to adjust the focal laws. This enables the fetal heart rates of all of the fetuses to be simultaneously and continuously monitored even when the fetuses move. In addition, this avoids having to reposition the single transducer (and belt) to accommodate for movement of the fetuses.

Figure 8:
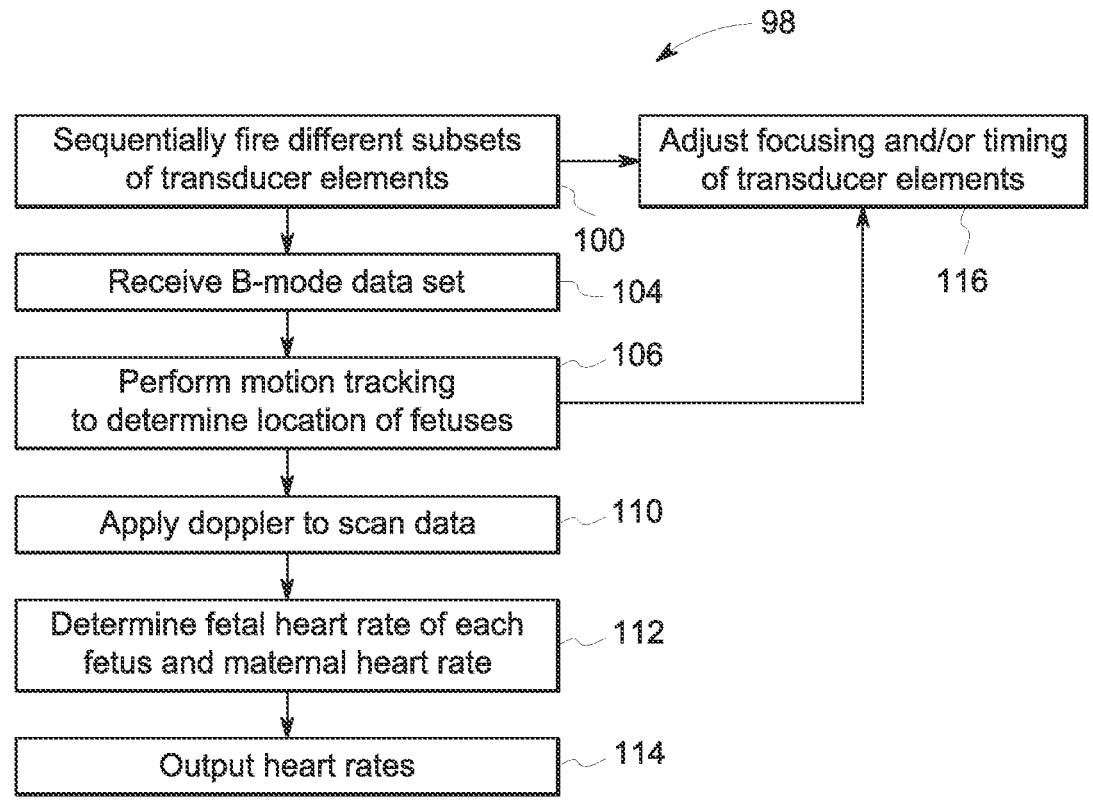
FIG. 8 is a flow chart of a method for simultaneously monitoring fetal heart rate in a plurality of fetuses in a uterus (e.g., utilizing optical flow vector-based tracking), in accordance with aspects of the present disclosure.
Figure 9:
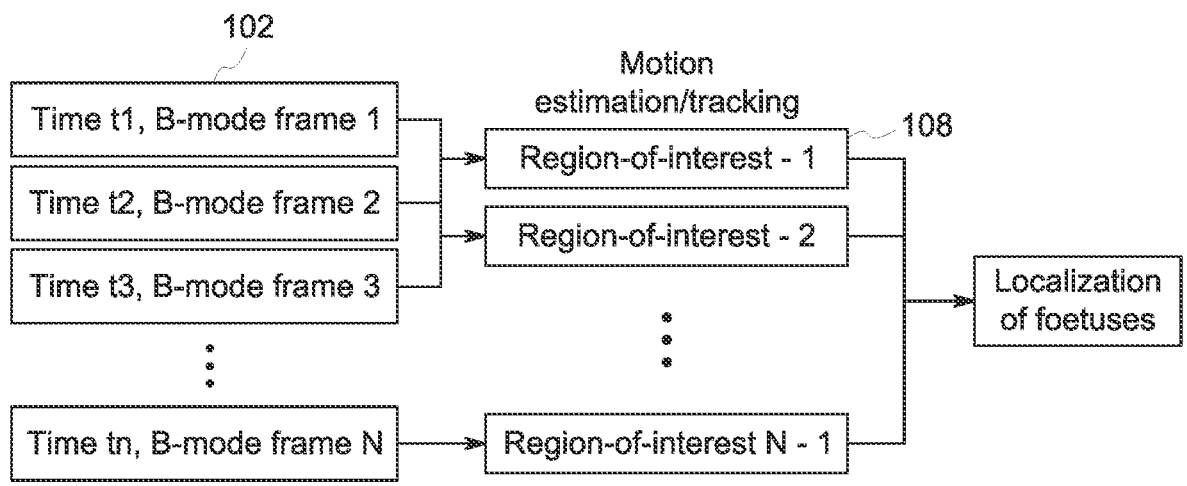
FIG. 9 is a schematic diagram of determining respective locations of fetuses according to the method in FIG. 8, in accordance with aspects of the present disclosure.

FIG. 8 is a flow chart of a method 98 for simultaneously monitoring fetal heart rate in a plurality of fetuses in a uterus (e.g., utilizing inter-frame motion estimation metrics from B-mode images). In certain embodiments, inter-frame motion estimation metrics from B-mode images, such as template-matching, phase-based or optical flow vector-based tracking, may be utilized to localize the fetuses. The method 98 may be performed by the control panel 36 (e.g., processing component 44) of the ultrasound system 10 in FIG. 1. The method 98 includes sequentially firing different subsets of transducer elements from a single transducer (e.g., transducer 14 in FIG. 2) to capture scan data (e.g., B-mode data) (block 100). In this embodiment, the ultrasound system is operating in B-mode mode, thus, individual rows of transducer elements are sequentially fired with each subsequent fired row being adjacent to the previously fired row. Thus, as illustrated in FIG. 9, different B-mode frames or B-mode lines 102 (e.g., B-mode frame 1 to B-mode frame N) will be acquired at different sequential time points (e.g., Time t1 to Time tn). In particular, the single transducer receives signals (e.g., control signals) for sequentially firing the different subsets of transducer elements for transmission and reception. As noted above, the firing sequence continues until each transducer element has been fired or triggered. Returning to FIG. 8, the method 98 also includes receiving or obtaining the sub-B-mode data from the single transducer (block 104). B-mode image data is acquired along multiple planes utilizing transducer elements from the array 58.

The method 98 further includes performing segmentation of region of interest (ROI) (e.g., for motion estimation/tracking) on the B-mode data acquired over time to determine a respective location (e.g., source location) of each fetus (e.g., fetal heart) of multiple fetuses disposed within the uterus of a patient (block 106). As depicted in FIG. 9, a respective ROI 108 is determined for each adjacent pair of B-mode frames 102. By tracking changes between subsequent frames or in a sequence of frames, the sources (i.e., of fetal motion) are identified. For example, for B-mode frame 1 and B-mode frame 2, ROI-1 is determined. For B-mode frame 2- and B-mode frame 3, ROI-2 is determined. The process continues for obtaining respective ROIs 108 for pair of adjacent B-mode frames 102. The ROIs 108 may be utilized to localize each of the fetuses. Segmentation of ROIs, is performed by estimating the inter-frame motion metrics from B-mode images, by template-matching, phase-based or optical flow vector-based tracking.

The method 98 still further includes applying Doppler shift to the scan data (block 110). Upon applying the Doppler shift, the method 98 includes determining a respective fetal heart rate for each fetus in the uterus and the maternal heart rate of the patient (block 112). The maternal heart rate is distinguishable from the fetal heart rates since the location of the maternal heart rate will remain stationary relative to the single transducer. Thus, the maternal heart rate will not be confused with the fetal heart rates. The method 98 also includes outputting the heart rates (e.g., fetal heart rates and maternal heart rate) (block 114). For example, the heart rates may be shown on a display of the ultrasound system (e.g., display 47 in FIG. 1) or a remote display.

In certain embodiments, when one or more of the fetuses in the uterus moves, the method 98 includes adjusting (e.g., via one or more algorithms) the focusing of the transducer elements and/or the timing (e.g. of the firing or triggering) of the transducer elements (block 116). This enables the fetal heart rates of all of the fetuses to be simultaneously and continuously monitored even when the fetuses move. In addition, this avoids having to reposition the single transducer (and belt) to accommodate for movement of the fetuses.

Figure 10:
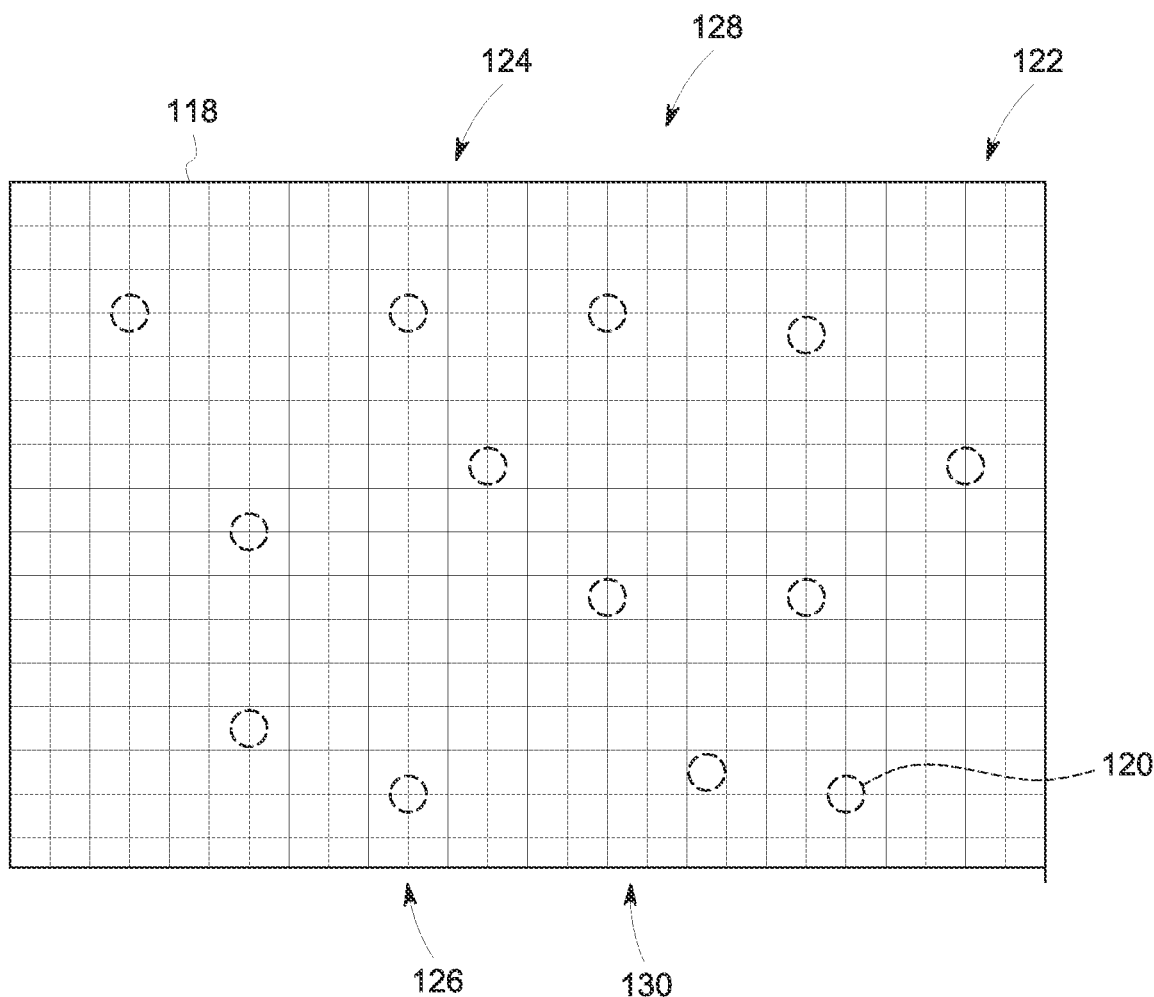
FIG. 10 is a schematic diagram of a disposable undergarment having sensors coupled to it forming a maternal fetal monitor, in accordance with aspects of the present disclosure.

FIG. 10 is a schematic diagram of a disposable undergarment 118 having sensors 120 coupled to it forming a maternal fetal monitor 122. The disposable undergarment 118 is similar to the belt (e.g., belt 52 in FIGS. 2-5 above). The disposable undergarment 118 is configured to be disposed about the abdomen of the patient (e.g., such as flexible belt 54 in FIG. 5 disposed about an abdomen 56 of the pregnant patient 18). A plurality of sensors 120 are coupled to the disposable undergarment 118. The sensors 120 may be of the same type or different. The sensors 120 may include one or more of ultrasound transducers, temperature sensors, pulse oximeters, pressure sensors, and other sensor types. The sensors 120 may detect multiple maternal and fetal parameters such as heart rate, blood pressure, respiration, temperature, pulse oximetry, uterine contractions, and other parameters. The sensors 120 are disposed on an inner surface of the disposable undergarment and oriented so that the detecting components of the sensors 120 face the abdomen and/or the back. Together, the disposable undergarment 118 and the sensors form the maternal fetal monitor 122. The disposable undergarment 118 may be made of a biocompatible and non-allergenic material. The disposable undergarment 118 may be designed to be comfortable on the patient. For example, the disposable undergarment may be made of a mesh material (e.g., similar to the material utilized with postpartum underwear) that is thin, soft, breathable, and cool. The disposable undergarment 118 may also be stretchy so as to conform to the different sizes of patients. In certain embodiments, the disposable undergarment 118 may have full openings 124, 126 on respective ends 128, 130 (e.g., superior and inferior ends) to enable the disposable undergarment 118 to be slid along the patient's body until is disposed about the abdomen. In certain embodiments, the disposable undergarment may be adjustable for fit and wrapped around the abdomen of the patient (e.g., similar to abdominal binders) and secured via fasteners (e.g., hook and loop fasteners). The sensors 120 may be coupled to the disposable undergarment prior to or after placing the disposable undergarment 118 about the patient.

The maternal fetal monitor 122 may improve signal detection due to the multiple points of detection by the sensors 120 disposed on the disposable undergarment 118. In addition, the sensors 120 may be wireless and communicate data to a remote device (e.g., monitoring device) for processing and/or display. Since the sensors 120 are wireless, it provides more freedom due to a lack of cables. Further, no cleaning is needed since the undergarment 118 is disposable.

Technical effects of the disclosed subject matter include providing systems and methods for simultaneously monitoring maternal heart rate and multiple fetal heart rates of multiple fetuses disposed within a single uterus of a patient. In particular, a single transducer may be utilized to continuously monitor the maternal heart rate and the multiple fetal heart rates without having to adjust a position of the single transducer even if one or more of the fetuses move. The ultrasound system is configured to determine a location of each fetus (in particular, a heart of each fetus) of the multiple fetuses and focus on each fetus to determine/measure a fetal heart rate of each fetus while also determining the maternal heat rate. This can be accomplished without confusing the maternal heart rate with the fetal heart rates. The ultrasound system utilizes different algorithms, described in FIGS. 6-9, to change where to focus with the transducer elements and/or a timing of data acquisition with the transducer elements to keep locked on to the fetuses for monitoring without having to change the position of the single transducer. The single transducer provides a more comfortable experience for the patient during the monitoring of the different heart rates and avoids having to utilize multiple bulky ultrasound transducers that need to be often readjusted.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An ultrasound system, comprising:
a single transducer, comprising:
a flexible substrate; and
an array of transducer elements disposed on the flexible substrate and configured to be disposed on an abdomen of a subject having one or more fetuses disposed within a single uterus and to acquire scan data; and
a processor coupled to the single transducer and configured to receive the scan data, to determine a respective location of each fetus of the one or more fetuses based on the scan data, and to determine a respective fetal heart rate of each fetus of the one or more fetuses based on the scan data with Doppler shifts applied, wherein the processor is configured to provide signals to the single transducer to cause different subsets of the transducer elements to sequentially fire for capturing sub-aperture full matrix capture (FMC) data, to receive the sub-aperture FMC data, and to perform total focusing method reconstruction to determine the respective location of each fetus of the one or more fetuses based on the sub-aperture FMC data, and wherein the processor is configured to determine the respective location of each fetus of the one or more fetuses prior both to applying the Doppler shifts to the scan data and to determining the respective fetal heart rate of each fetus of the one or more fetuses based on the scan data with the Doppler shifts applied.

2. The ultrasound system of claim 1, wherein the array of transducer elements is configured to determine a maternal heart rate of the subject based on the scan data.

3. The ultrasound system of claim 1, wherein the processor is configured to adjust a focusing of the transducer elements and a timing of data acquisition from the different subsets of the transducer elements both to keep locked on the one or more fetuses and to maintain monitoring of the respective fetal heart rate of each fetus upon movement of the one or more fetuses without adjusting a position of the single transducer.

4. The ultrasound system of claim 1, wherein the flexible substrate comprises a stretchable mesh.

5. The ultrasound system of claim 4, wherein the stretchable mesh has respective openings on a superior end and an inferior end to enable the flexible substrate to be slid along the subject to be disposed on the abdomen.

6. The ultrasound system of claim 1, wherein the single transducer is coupled to the processor via a wired connection.

7. The ultrasound system of claim 1, wherein the single transducer is coupled to the processor via a wireless connection.

8. An ultrasound system, comprising:
a transducer, comprising;
a flexible substrate; and
an array of transducer elements disposed on the flexible substrate and configured to be disposed on an abdomen of a subject having one or more fetuses disposed within a single uterus and to acquire scan data for determining a respective fetal heart rate of each fetus of the one or more fetuses based on the scan data; and
a processor coupled to the transducer and configured to provide signals to the transducer to cause different subsets of the array of transducer elements to sequentially fire for capturing a B-mode dataset, to receive the B-mode dataset, to perform segmentation of regions of interest utilizing inter-frame motion estimation metrics to determine a respective location of each fetus of the one or more fetuses based on the B-mode dataset, and to determine a respective fetal heart rate of each fetus of the one or more fetuses based on the scan data with Doppler shifts applied, and wherein the processor is configured to determine the respective location of each fetus of the one or more fetuses prior both to applying the Doppler shifts to the scan data and to determining the respective fetal heart rate of each fetus of the one or more fetuses based on the scan data with the Doppler shifts applied.

9. The ultrasound system of claim 8, wherein the processor is configured to determine a respective location of each fetus of the one or more fetuses based on the scan data.

10. The ultrasound system of claim 8, wherein the processor is configured to determine a maternal heart rate of the subject based on the scan data.

11. The ultrasound system of claim 8, wherein the flexible substrate comprises a stretchable mesh.

12. The ultrasound system of claim 11, wherein the stretchable mesh has respective openings on a superior end and an inferior end to enable the flexible substrate to be slid along the subject to be disposed on the abdomen.

13. A method for simultaneously monitoring fetal heart rate in a plurality of fetuses in a uterus, comprising:
providing, via a processor, signals to a single transducer to cause different subsets of transducer elements of the single transducer to sequentially capture scan data, wherein the single transducer comprises a flexible substrate and a flexible array having the transducer elements disposed on the flexible substrate, and wherein providing the signals to the single transducer comprises providing the signals to the single transducer to cause the different subsets of the transducer elements to sequentially capture sub-aperture full matrix capture (FMC) data;
receiving, at the processor, the scan data and the sub-aperture FMC data;
determining, via the processor, a respective location of each fetus of the plurality of fetuses based on the scan data, wherein determining the respective location comprises performing total focusing method reconstruction to determine the respective location of each fetus of the plurality of fetuses based on the sub-aperture FMC data;

applying, via the processor, Doppler shifts to the scan data; and determining, via the processor, a respective fetal heart rate of each fetus of the plurality of fetuses based on the scan data with the Doppler shifts applied, wherein the respective location of each fetus of the plurality of fetuses is determined prior both to applying the Doppler shifts to the scan data and to determining the respective fetal heart rate of each fetus of the plurality fetuses based on the scan data with the Doppler shifts applied.

14. The method of claim 13, comprising adjusting, via the processor, a focusing of the transducer elements and a timing of data acquisition from the different subsets of the transducer elements both to keep locked on the plurality of fetuses and to maintain monitoring of the respective fetal heart rate of each fetus upon movement of the plurality of fetuses without adjusting a position of the single transducer.

* * * * *